United States Patent [19]

Reichenbach et al.

[11] Patent Number: 5,658,254
[45] Date of Patent: Aug. 19, 1997

[54] SYRINGE HAVING SAFETY NEEDLE SHIELD

[75] Inventors: Eric P. Reichenbach, Pompton Plains; Robert B. Odell, Franklin Lakes, both of N.J.

[73] Assignee: Becton, Dickinson and Company, Franklin Lakes, N.J.

[21] Appl. No.: 414,850

[22] Filed: Mar. 31, 1995

[51] Int. Cl.$^6$ ............................................. A61M 5/32
[52] U.S. Cl. ........................ 604/192; 604/110; 604/198
[58] Field of Search ............................ 604/192–8, 263, 604/164

[56] References Cited

U.S. PATENT DOCUMENTS

| | | | |
|---|---|---|---|
| 4,573,976 | 3/1986 | Sampson et al. | 604/198 |
| 4,631,057 | 12/1986 | Mitchell | 604/198 |
| 4,743,233 | 5/1988 | Schneider | 604/192 |
| 4,976,702 | 12/1990 | Andrews et al. | 604/198 |
| 5,024,660 | 6/1991 | McNaughton | 604/110 |
| 5,127,910 | 7/1992 | Talonn et al. | 604/198 |
| 5,141,500 | 8/1992 | Hake | 604/198 |
| 5,154,698 | 10/1992 | Compagnucci et al. | 604/110 |
| 5,217,437 | 6/1993 | Talonn et al. | 604/198 |
| 5,304,149 | 4/1994 | Morigi | 604/192 |
| 5,312,370 | 5/1994 | Talonn et al. | 604/198 |
| 5,342,309 | 8/1994 | Hausser | 604/110 |
| 5,385,555 | 1/1995 | Hausser | 604/192 |

*Primary Examiner*—Sam Rimell
*Assistant Examiner*—Robert V. Racunas
*Attorney, Agent, or Firm*—John L. Voellmicke

[57] ABSTRACT

A safety syringe assembly includes a hypodermic syringe having a syringe barrel with opposed proximal and distal ends. A needle cannula is mounted to the distal end of the barrel. A collar mounted around the syringe barrel includes at least one radially inwardly directed recess. A safety shield is positioned over the syringe barrel for telescoping movement from a proximal position where the needle cannula is exposed to a distal position where the syringe safety shield protectively surrounds the needle cannula. The safety shield is rotatable with respect to the barrel when the safety shield is in its proximal position. The safety shield includes an inside surface having at least one inwardly directed projection sized and positioned to pass through the recess in the collar when the safety shield is rotated with respect to the barrel to align the projection and the recess. When alignment is achieved the safety shield can be moved form the proximal position to the distal position. The collar and the projection prevent movement of the safety shield from the proximal position when the projection and the recess are not aligned.

17 Claims, 9 Drawing Sheets

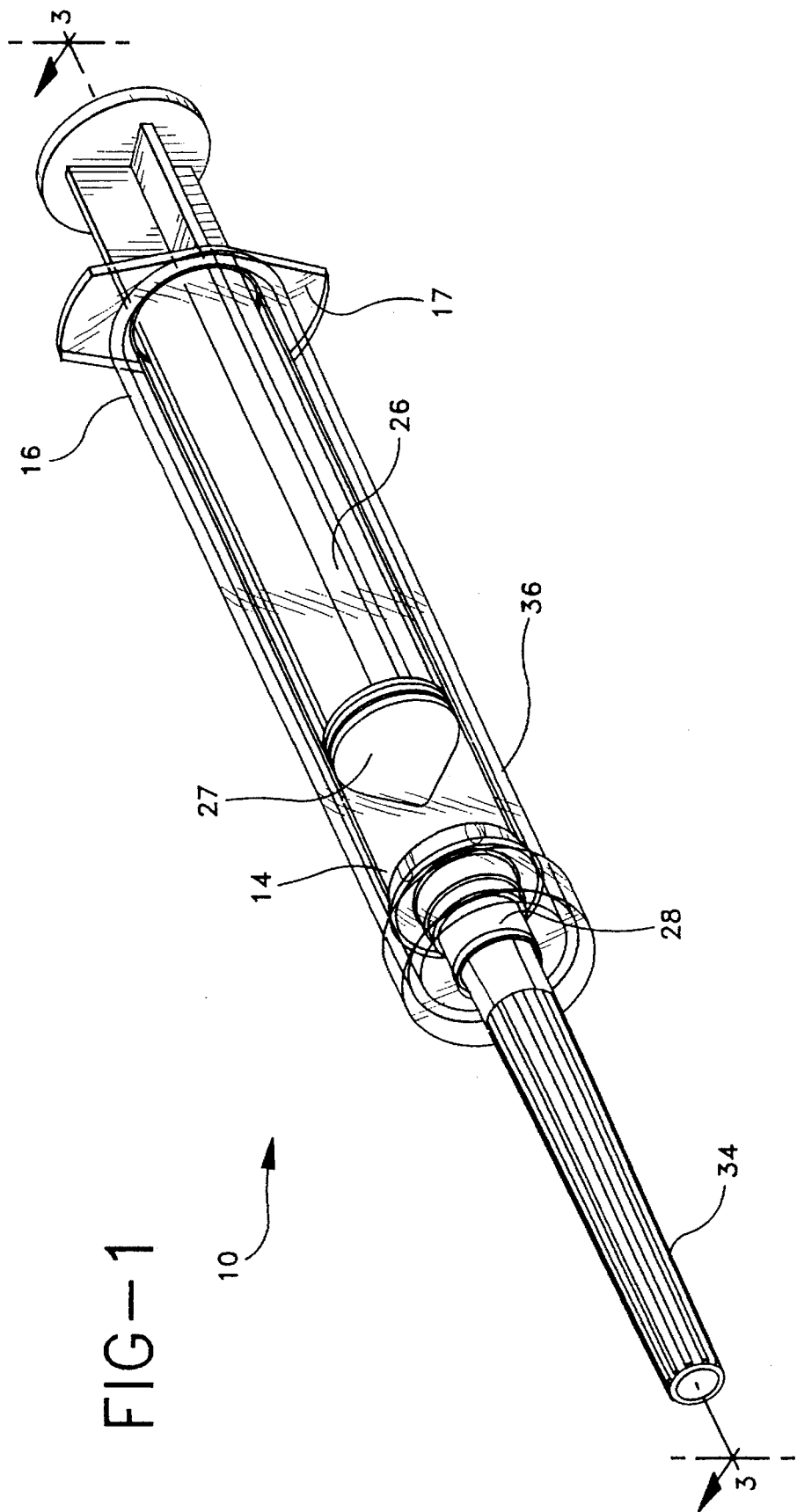

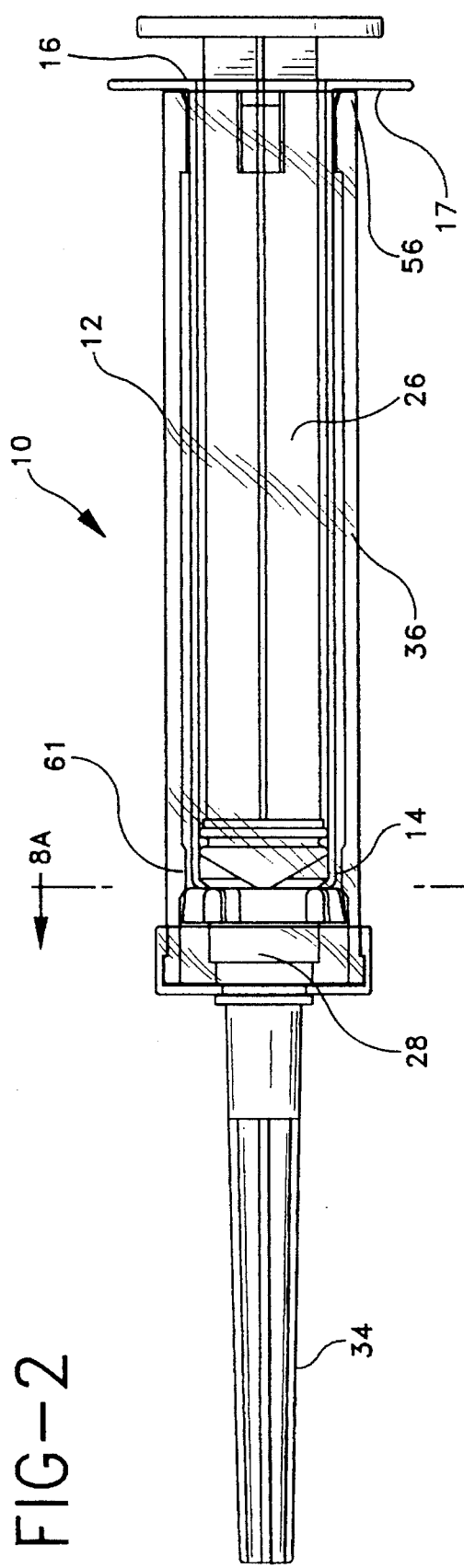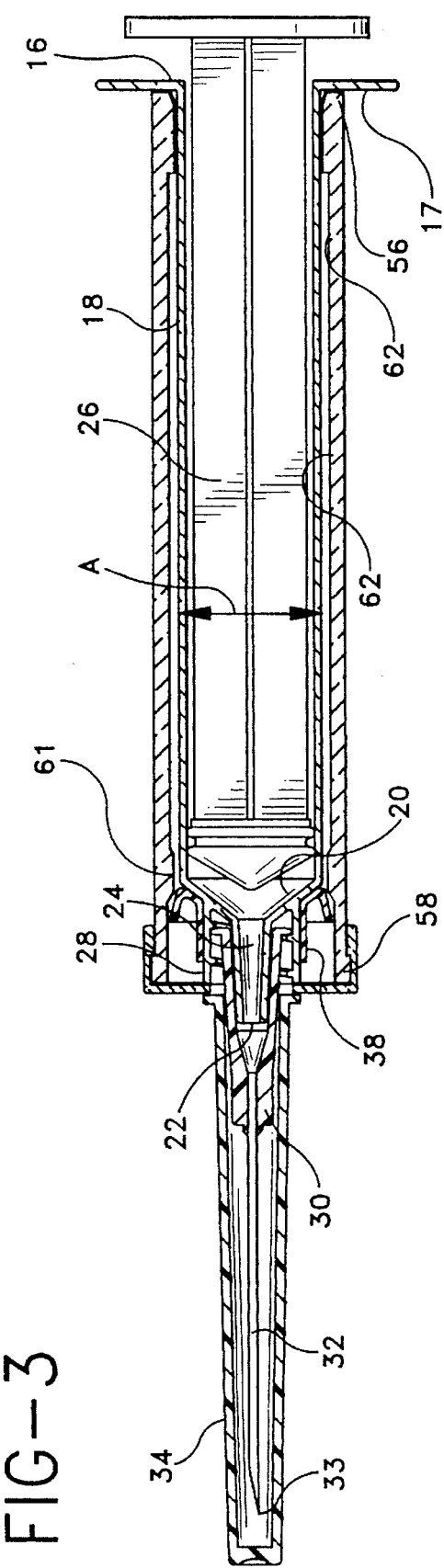

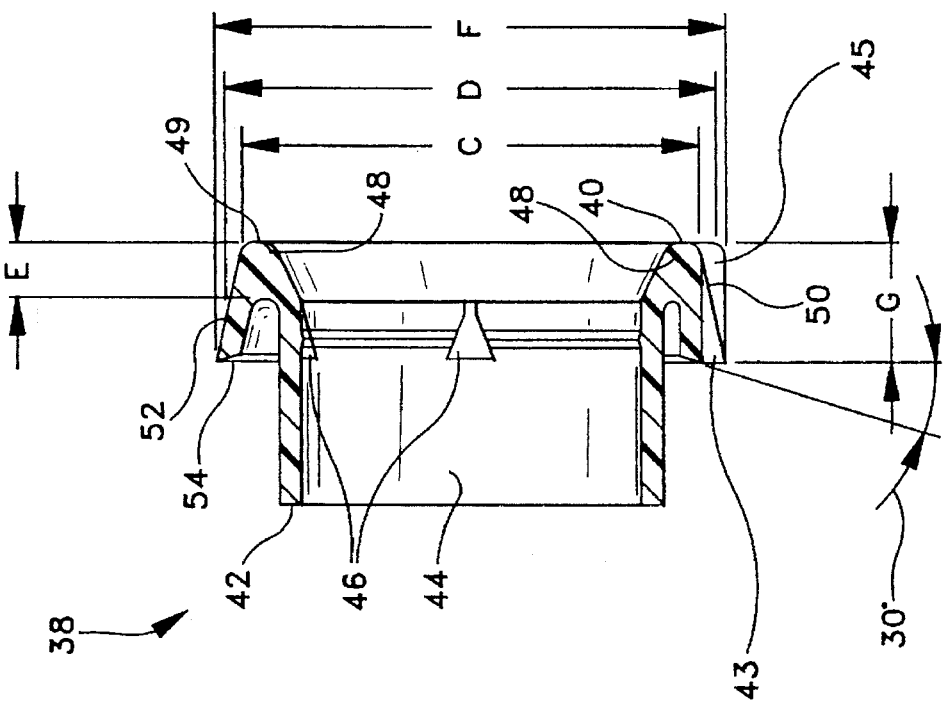
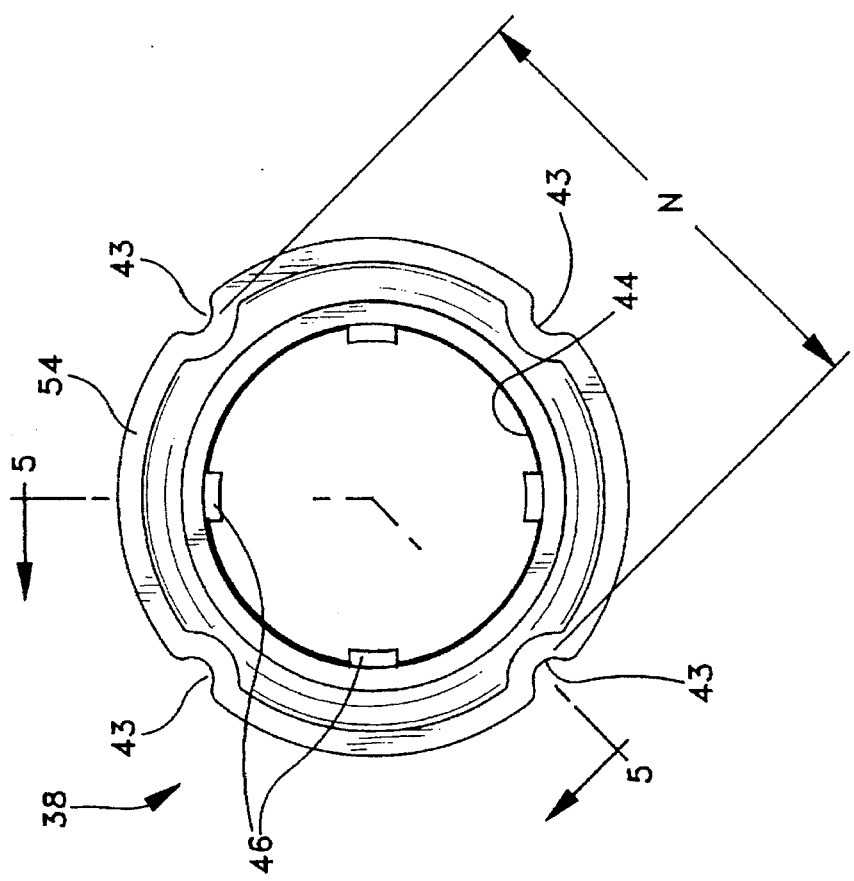

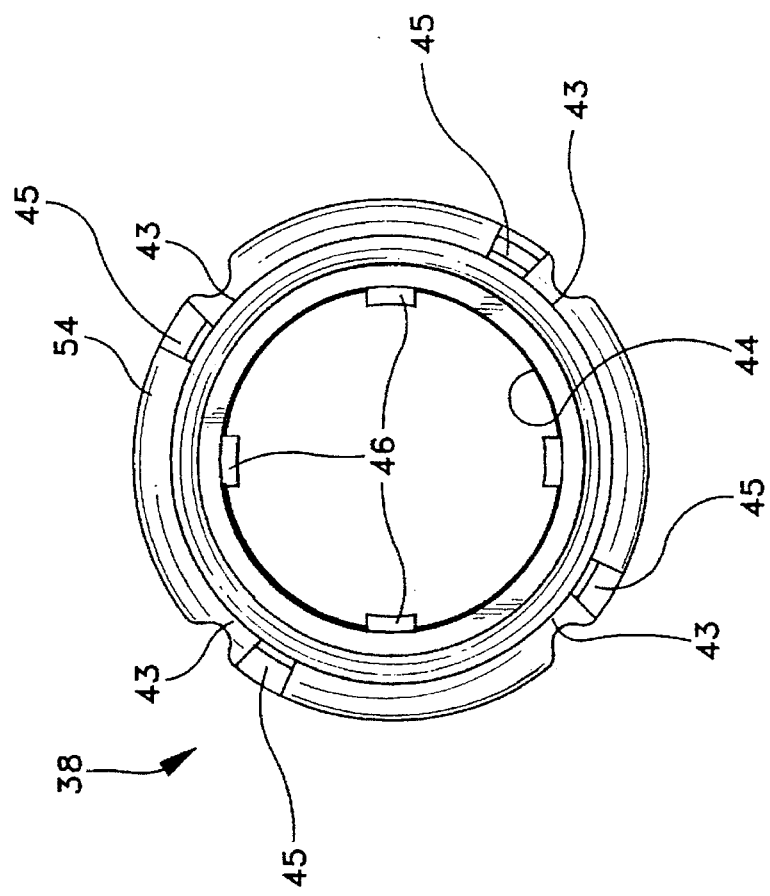
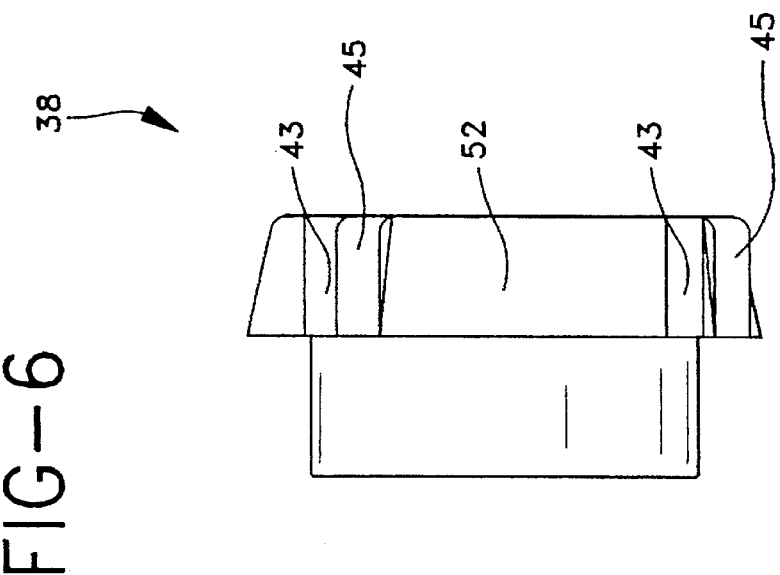

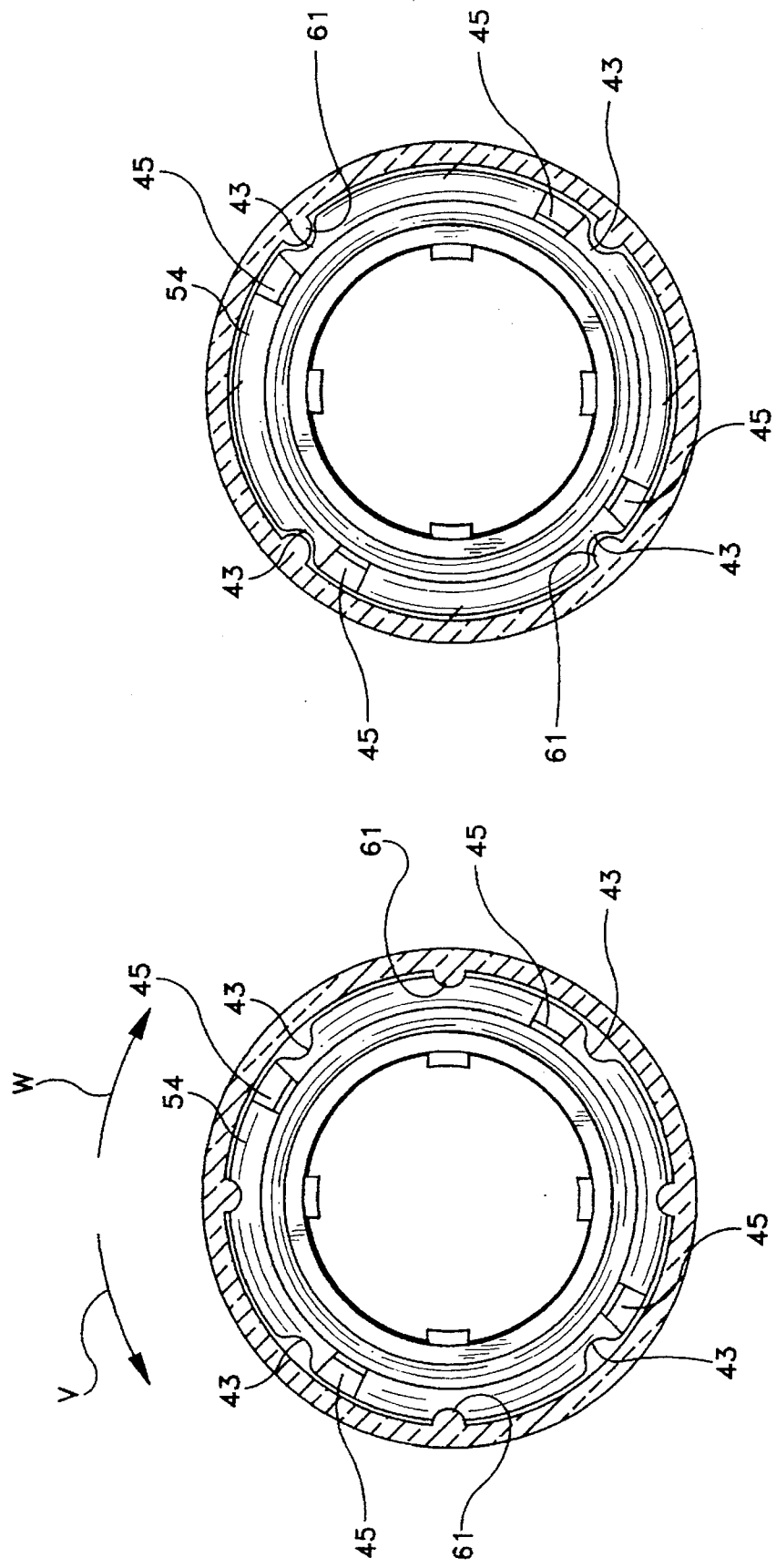

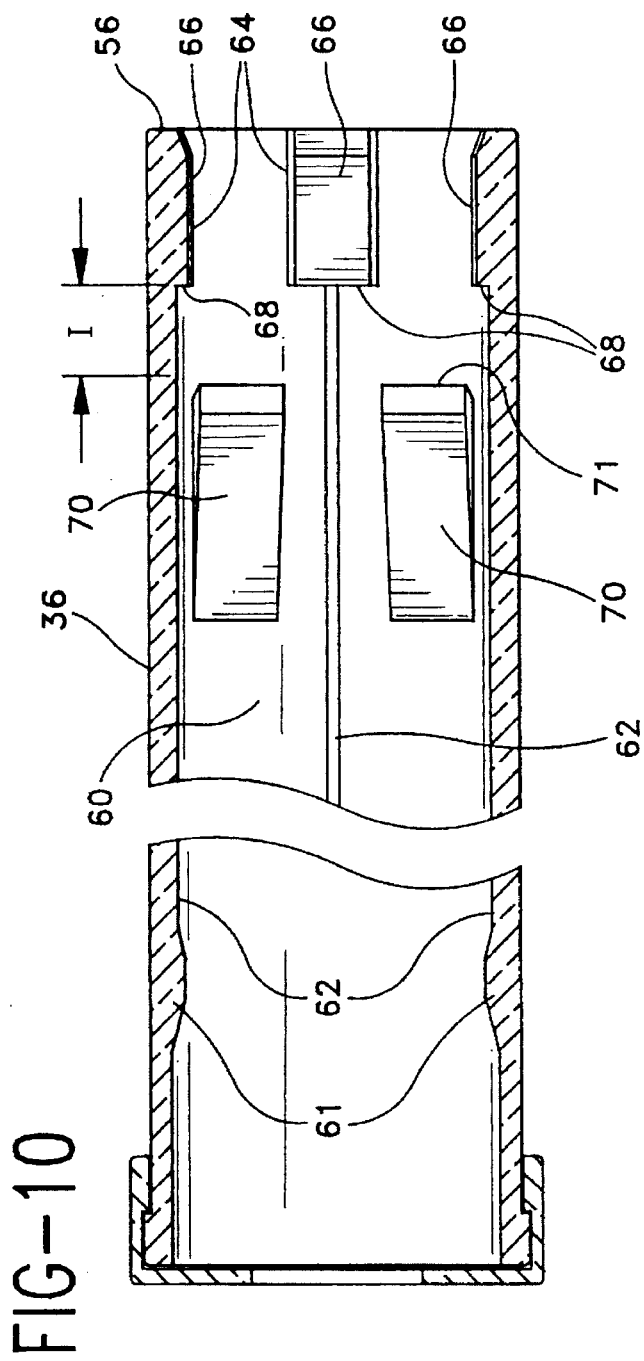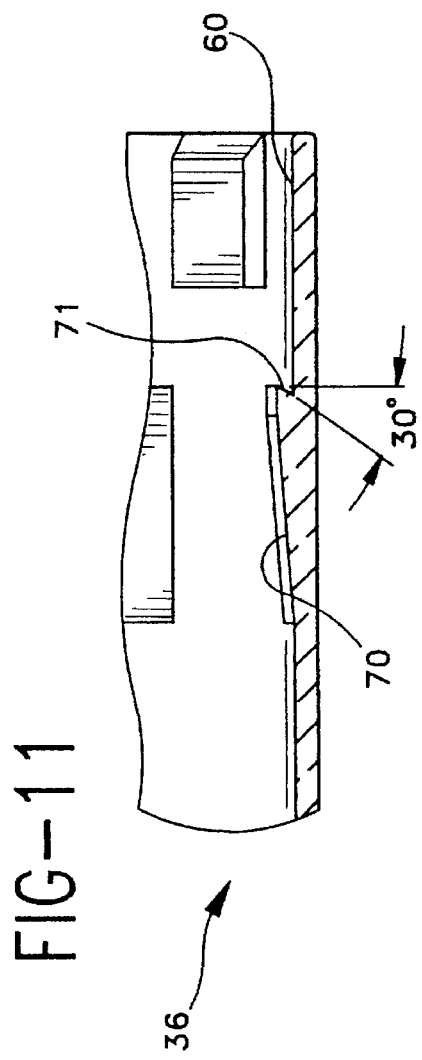
FIG-10
FIG-11

SYRINGE HAVING SAFETY NEEDLE SHIELD

BACKGROUND OF THE INVENTION

1. Field of the Invention

The subject invention relates to a hypodermic syringe having a sharp needle cannula and a rigid protective shield positioned over the syringe barrel for movement from a position which exposes the needle cannula to a position which surrounds the needle cannula.

2. Description of the Prior Art

Hypodermic syringes typically have a needle shield removably mounted over the needle cannula to avoid accidental needle sticks and to prevent damage to the needle before use. The needle shield can be safely removed and discarded when the hypodermic syringe is about to be used.

Accidental needle sticks occurring after the needle cannula has been used pose a greater health risk, because the used needle cannula may be contaminated. Most health care facilities provide sharps receptacles into which a used hypodermic syringe may be safely deposited. However, the hypodermic syringe is not always used near a sharps receptacle, and the needs of a patient may prevent the health care worker from traveling to the sharps receptacle immediately after using the hypodermic syringe.

The prior art includes hypodermic syringes with a safety shield telescoped over the syringe barrel and movable between a proximal position where the needle cannula is exposed and a distal position where the needle cannula is surrounded. The prior art safety shield is releasably retained in its proximal position until after the needle cannula is used. The safety shield then is moved distally on the syringe barrel to protectively enclose the needle cannula for preventing accidental needle sticks. The shield is either locked in the extended position or releasably retained in this position.

The prior art focuses on structures for holding the safety shield in its distal needle protecting position. Many structures are taught which involve structure on the distal end of the syringe barrel and the proximal end of the safety shield. However, the prior art gives less attention to releasably retaining the safety shield in its proximal needle exposing position. The safety shield must be held to the syringe barrel with enough force to prevent it from becoming dislodged during normal use of the syringe. However, the force must not be so high that the shield cannot be easily moved from the proximal position to the distal needle protecting position. Some designs rely on an interference fit between structure on the inside diameter of the proximal end of the safety shield and the outside diameter of the proximal end of the syringe barrel. However, the frictional engagement places stresses in the safety shield and the barrel, and, over time, the plastic material creeps and the retaining force is reduced. Also, the frictional interference fits are very tolerance dependent. Accordingly, manufacturers may have to design the part initially to require more force to move the safety shield than is ideal, knowing that over time the force will gradually be reduced. Other prior art devices use canitilevered projections from the needle shield to engage a groove or recesses in the proximal end of the syringe barrel. This structure reduces the problems mentioned above, however, it is still subject to creep and tolerance dependency. Also, providing structure on the proximal end of the syringe barrel to accomplish the releasable retention of the safety shield creates additional manufacturing difficulty because both ends of the syringe barrel must have tightly controlled dimensions, with the distal end of the barrel controlling the safety shield in its extended position and the proximal end of the barrel controlling the safety shield in its retracted proximal position. Also, structure on the proximal end of the syringe barrel can greatly increase manufacturing costs due to the injection molding process wherein it becomes difficult to remove the syringe from the mold because of this structure. The mold can, at much greater cost, be made to split along the longitudinal axis of the barrel or have cam actuated elements to allow easy removal of the molded barrel. Without the more complex mold, the structure on the barrel may have to be so small to enable the barrel to be removed from the mold that it may not be as effective as desired.

Although the prior art provides many syringes having safety shields and many structures to hold the safety shield in the extended needle protecting position and to releasably retain the safety shield in its proximal needle exposing position, there is still a need for simple, straight-forward easy-to-manufacture syringe having a safety shield wherein both the extended and the retracted position of the safety shield are controlled by structure on the distal end of the syringe barrel using a structure that does not subject the safety shield and the syringe barrel to great stresses while the syringe is in storage with the safety shield in its proximal position with respect to the syringe barrel.

SUMMARY OF THE INVENTION

The subject invention is directed to a safety syringe assembly including a hypodermic syringe having a syringe barrel with opposed proximal and distal ends and a needle cannula mounted on the distal end of the syringe barrel. A collar is mounted around the distal end of the syringe barrel. The collar includes at least one radially inwardly directed recess. A safety shield is positioned over the syringe barrel for telescoping movement from a proximal position where the needle cannula is exposed to a distal position where the safety shield protectively surround the needle cannula. The safety shield is rotatable with respect to the barrel when the safety shield is in its proximal position. The safety shield includes an inside surface having at least one inwardly directed projection sized and positioned to pass through the recess in the collar when the safety shield is rotated with respect to the barrel to align the projection in the safety shield and the recess in the collar and the safety shield is moved from the proximal position to the distal position. The collar and the projection prevent movement of the safety shield from the proximal position when the projection and the recess in the collar are not aligned. Structure is provided for locking engagement of the collar and the safety shield for locking the safety shield in a distal position, wherein the locking engagement can be achieved solely upon axial movement of the safety shield distally with respect to the barrel.

Means for locking the safety shield in the distal position can include the collar having a stop wall projecting outwardly from the syringe barrel and at least one deflectable lock wall projecting distally and outwardly from the collar. The safety shield includes at least one stop block projecting inwardly therefrom and being engageable with the stop wall of the collar for preventing removal of the safety shield from the syringe barrel when the shield is in the distal position. The safety shield further includes at least one locking tooth dimensioned and disposed to generate inward deflection of the locking wall of the collar during telescoping movement of the safety shield from the proximal position toward the distal position. The locking tooth being spaced distally from the stop block a sufficient distance to enable engagement of the lock wall and the stop wall of the collar between the locking tooth and the stop lock of the safety shield. The locking tooth is configured to lockably engage the deflectable lock wall to prevent proximal movement of the safety shield from its locked distal position.

BRIEF DESCRIPTION OF THE DRAWINGS

FIG. 1 is a perspective view of a hypodermic syringe having a safety shield in accordance with the subject invention.

FIG. 2 is a side elevational view of the syringe assembly of FIG. 1.

FIG. 3 is a cross-sectional view of the syringe assembly of FIG. 1 taken along line 3—3.

FIG. 4 is an end elevational view of the collar of the syringe assembly.

FIG. 5 is a cross-sectional view of the collar of FIG. 4 taken along line 5—5.

FIG. 6 is a side elevational view of the collar of the syringe assembly.

FIG. 7 is an end elevational view of the collar showing the end opposite of the end illustrated in FIG. 4.

FIG. 8A is a cross-sectional view of the syringe assembly of FIG. 2 taken along line 8—8 illustrating the safety shield retained by the collar in its proximal position.

FIG. 8B is the syringe assembly of FIG. 8A with the safety shield rotated to align the projections in the safety shield with the recesses in the collar so that the safety shield may be advanced from the proximal position.

FIG. 10 is a partial cross-sectional view of the safety shield of FIG. 9 taken along line 10—10.

FIG. 11 is a partial cross-sectional view of the safety shield of FIG. 9 taken along line 11—11.

DETAILED DESCRIPTION OF THE INVENTION

Figure 9B:
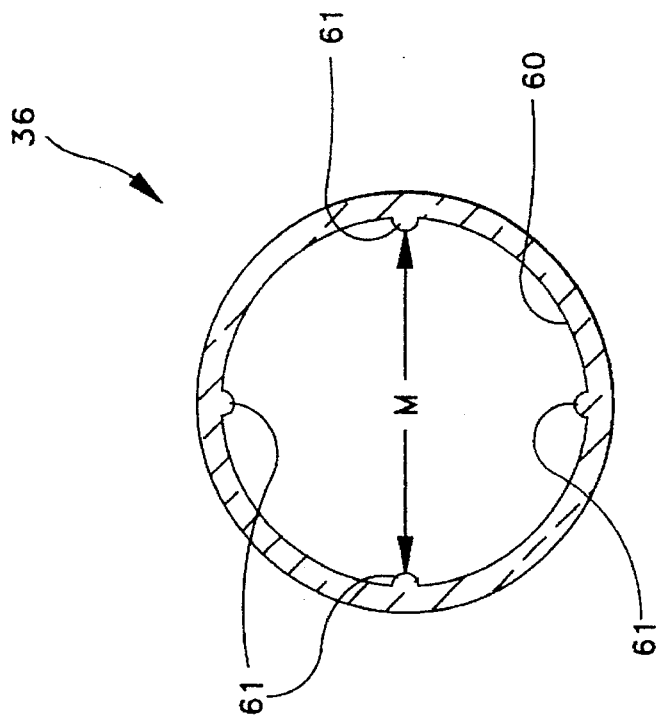
FIG. 9B is a distal elevational view of a safety shield with end cap removed.

A hypodermic syringe in accordance with the invention is illustrated in FIGS. 1–12 and is identified generally by the numeral 10. Hypodermic syringe 10 includes a generally cylindrical syringe barrel 12 having a distal end 14, an open proximal end 16 and a generally cylindrical wall 18 extending therebetween to define a fluid receiving chamber 20. Finger flange 17 is positioned at the open proximal end of the barrel. Cylindrical wall 18 of syringe barrel 12 defines an outside diameter "A" along most of its length, as shown in FIG. 3. With further reference to FIG. 3, the distal end of syringe barrel 12 preferably includes a tip 22 having a fluid passage 24 extending therethrough and communicating with chamber 20. A plunger 26 is disposed in sliding fluid-tight engagement with cylindrical wall 18 of syringe barrel 12. Sliding movement of plunger 26 toward distal end 14 causes fluid in chamber 20 to be expelled through passage 24. Conversely, sliding movement of plunger 26 away from distal end 14 of syringe barrel 12 will draw fluid through passage 24 and into chamber 20. The plunger is preferably made of two-piece construction with a resilient elastomeric element, such as stopper 27, at its distal end to effectively seal the barrel. However, one-piece plungers are known in the art and are within the purview of the present invention.

The distal end of syringe barrel 12 further includes a locking luer-type collar 28 disposed in spaced concentric relationship around tip 22. Luer collar 28 includes an array of internal threads to enable threaded mounting of a needle hub 30 between collar 28 and tip 22. A needle cannula 32 is securely mounted to needle hub 30 and is in fluid communication with passage 24 and chamber 20.

Needle cannula 32 includes sharp tip 33. To prevent accidental needle sticks prior to use of hypodermic syringe 10, a needle shield 34 is removably mounted over needle cannula 32. Needle shield 34 can be removed from hypodermic syringe 10 immediately prior to use to reduce the potential for accidental needle sticks prior to using the hypodermic syringe.

A safety shield 36 and a collar 38 are provided to help avoid needle sticks after using hypodermic syringe 10. Collar 38 is a generally annular structure preferably unitarily formed from a thermoplastic material and having opposed proximal and distal ends 40 and 42 respectively. An inner surface 44 extends between ends 40 and 42 and is preferably dimensioned to tightly engage outer surface of luer collar 28 at distal end 14 of syringe barrel 12. As shown most clearly in FIG. 5, inner surface 44 of collar 38 preferably includes a plurality of spaced apart barbs 46 pointing inwardly and in a generally distal direction. The barbs enable collar 38 to be slid in a distal to proximal direction over distal end 14 of syringe barrel 12. However barbs 46 bite into the thermoplastic material of luer collar 28 to prevent removal of collar 38 from syringe barrel 12 in a proximal-to-distal direction.

It is within the purview of the present invention to include a collar which is integrally molded with the syringe barrel or attached in other ways to the syringe barrel. For example, the collar may be attached to the cylindrical wall of the syringe barrel. For syringe barrels not having a locking luer-type collar, such as locking luer-type collar 28, the collar may be attached directly to the tip, such as tip 22. Also, an intermediate structure may be provided. This intermediate structure could attach to the tip and provide a larger cylindrical surface, spaced from the tip, onto which a collar, such as collar 38, can be attached.

Collar 38 is characterized by a solid annular stop wall 48 extending distally from proximal end 40. Stop wall 48 includes an outer circumferential surface which expands frusto-conically outwardly at locations distally of proximal end 40 of locking collar 38. Thus, the proximal end 40 defines a minor outside diameter "C, as shown in FIG. 5, and an outside diameter "D". Minor outside diameter "C" at proximal end 40 of collar 38 exceeds outside diameter "A" of cylindrical wall 18 of syringe barrel 12. Thus, proximal end 40 extends radially outwardly beyond syringe barrel 12 as shown in FIG. 3. Solid annular stop wall 48 defines an axial tenth "E" which is selected to resist distally directed forces exerted on collar 38 by safety shield 36 as explained further herein. More particularly, the axial length of stop wall 48 and the frusto-conical shape of outer surface 50 will cause distally directed forces on collar 38 to urge collar 38 radially inwardly such that barbs 46 bite deeper into luer collar 28 at distal end 14 of syringe barrel 12.

Collar 38 further includes a resiliently deflectable lock wall 52 projecting distally and outwardly from stop wall 48 to define a major outside diameter "F" for locking collar 38. More particularly, resiliently deflectable lock wall 52 is spaced radially outwardly from portions of collar 38 disposed distally of annular stop wall 48 to form radially inward deflection of lock wall 52. The resiliently deflectable lock wall is preferably a substantially continuous conical wall as shown in FIGS. 4–6.

Returning to FIG. 5, resiliently deflectable lock wall 52 includes a distal end 54 of generally concave frusto-conical shape defining an angle of about 30° to a radius of collar 38. The concave configuration of distal end 54 functions as a ramp which urges deflectable lock wall 52 radially outwardly in response to distal-to-proximal forces exerted thereon.

Collar 38 should also include at least one radially inwardly directed recess. In this preferred embodiment, collar 38 includes four radially inwardly directed recesses 43. Optionally, the collar may also contain at least one radially directed protuberance adjacent to one side of the recess. In this preferred embodiment, collar 38 includes four radially directed protuberances 45. The function of recesses 43 and protuberances 45 will be explained in more detail hereinafter.

Safety shield 36 is an elongate tubular structure disposed in sliding telescoped relationship over syringe barrel 12. Safety shield 36 is preferably molded from thermoplastic material to include opposed proximal and distal ends 56 and 58 respectively, and an axial length greater than the length of needle cannula 32. The safety shield preferably includes an inner circumferential surface 60 having a plurality of shallow longitudinally extending ribs 62.

Safety shield 36 preferably includes a removable end cap 63 on its distal end 58. The end cap is provided to prevent finger contact with sharp tip 33 of the needle cannula after the shield is in its extended needle protecting position. The removable end cap also allows the syringe to be used for other procedures wherein the safety shield is in its fully extended needle protecting position. One such procedure would involve removal of the end cap and insertion of an evacuated tube into the safety shield until the syringe needle pierces the pierceable stopper of the evacuated tube so that blood in the syringe may be withdrawn from the syringe to the evacuated tube.

Safety shield 36 also includes at least one inwardly directed projection and in this preferred embodiment includes four inwardly directed projections 61 which are preferably substantially equally spaced from each other along inside surface 60 of the safety shield. Projections 61 and their interaction with recesses 43 on the collar are an important aspect of the present invention. It is important that during the use of the syringe assembly, for example, when filling the syringe through the needle cannula and administering an injection, that the safety shield be retained with sufficient force so that it does not move with respect to the syringe barrel. This is important since forces that would normally be applied to the barrel by the user's hands using an unshielded syringe are now being applied to the safety shield. If the safety shield is not sufficiently retained in its proximal position with respect to the barrel the normal use of the syringe will result in forces causing the safety shield to be dislodged possibly accidentally locked in the distal position before use of the syringe is completed. Satisfying this requirement is difficult since the structure provided must hold the safety shield in the proximal position with sufficient force to prevent its movement during the normal use of the syringe and with a retaining force that is not excessive so that it will not be extremely difficult to move the safety shield from the proximal position to the distal position. Accordingly, the more aggressively the safety shield is held in the proximal position, the more difficult it is to move to the distal position. Also, if the force holding the safety shield in the proximal position is not sufficient it will become dislodged during the normal use of the syringe. Designs using a frictional interference fit between the inside of the safety shield and the outside of the syringe are expensive because they require tight control of dimensional tolerances. Also, over time the stress created by the frictional interference fit between the inside diameter of the shield and the outside diameter of the barrel causes the plastic components to creep thus reducing the stress and the frictional force holding the syringe in the retracted position. Accordingly, a syringe which has an interference fit which is sufficient to hold the safety shield in its retracted position at the time of manufacture may not adequately hold the safety shield in the retracted position after a year on the shelf. To compensate, the manufacturer may make the interference fit tighter than is necessary in anticipation of the creeping of the plastic. However, if the syringe is used earlier, the safety shield will be more difficult to advance and if the syringe stays on the shelf for an extended period of time, the retention forces holding the shield in its retracted position may be less than desired.

Some designs use cantilevers projecting from the shield to provide the retention force. These designs appear to reduce the criticality of creeping of the plastic material, but do not eliminate it. Further, other designs rely on structure such as grooves or ribs on the proximal end of the syringe barrel. Such structure while conceptually interesting is expensive or extremely difficult to achieve, If the molded plastic syringe barrel, during its manufacturing process, is drawing axially out of the injection mold the structure on the proximal end of the barrel could be stripped away or damaged by the mold. In the alternative, this structure can be made so slight that it deflects upon removal of the barrel from the mold. However, this structure may not be sufficient for achieving adequate retention of the safety shield.

It is much more desirable to have the most critical structure involved with holding the safety shield in its proximal position, on the distal end of the syringe barrel, such as in the present invention. In the present invention a standard syringe barrel may be used and a collar provided which contains structure that cooperates with structure on the safety shield, for releasably retaining the shield in the proximal position and locking the shield in its distal needle protecting position. Also, it is desirable to retain the safety shield in its proximal position without aggressive press fits or a substantial amount of stress being placed in the components. Such a structure is provided by the present invention which functions as follows. When the safety shield of the present invention is in its retracted position as best illustrated in FIGS. 1–3 and 8A, inwardly directed projections 61 of safety shield 36 are positioned substantially behind collar 38. The safety shield cannot move from its proximal position because projections 61 which define diameter M in FIG. 9B which is smaller than diameter F of the collar and diameter M is preferably smaller than diameter D of the collar. In any event the collar blocks the distal motion of the safety shield by interfering with projection 61.

In order to advance the safety shield the user must rotate the safety shield to a position, as best illustrated in FIG. 8B, where projections 61 are aligned with recesses 43 in the collar. At this position the safety shield may be advanced axially distally toward its distal position. Preferably, diameter M defined by projections 61 is equal or less than diameter N defined by the root or base of recesses 43 so that the projections pass through the recesses with a slight interference or resistance. However, diameter M may be greater than diameter N so that projections 61 pass through recess 43 without interference. In order to stabilize the safety shield with respect to the barrel and hold it tightly enough so that the safety shield feels like it is part of the barrel during the normal use of the syringe it is preferred that in the proximal position, proximal end 56 of the safety shield abuts or touches flange 17 of the barrel and projections 61 press against resiliently deflectable locking wall 52 of the collar so that the safety shield is forcibly trapped between collar 38 and flange 17. This structure adequately retains the safety shield in a fixed position with respect to the barrel and provides an additional benefit in that when the user decides to move the safety shield to the distal position the user rotates the collar until the projections in the safety shield are aligned with the recesses in the collar. In the preferred design the pressure of the projections 61 against resilient deflectable locking wall 52 of the collar cause the projections to drop into the recesses 43 giving the user a tactile sensation that the alignment has been achieved. This structure eliminates the random hunting for the recesses and allows the user to be informed, by the structure, that alignment has been achieved.

Another optional feature of the present invention which enhances its use is a means for limiting the rotation of the safety shield with respect to the collar and barrel to less than 360° and preferably to about 90°. Means for limiting rotation can include structure or projections from the collar which interfere with the rotation of the sleeve with respect to the collar. Such structure is provided, in the preferred embodiment, by radially directed protuberances 45 projecting from proximal end 40 of collar 38. At least one protuberance is required and four are provided in this embodiment for improving the strength of the resistance to rotation. When rotating the shield counterclockwise with respect to the collar and barrel, illustrated as direction V in FIG. 8A, the safety shield will rotate until projections 61 are aligned with recesses 43. At that point further rotation in a counterclockwise direction will be resisted by contact with protuberances 45. At this point the shield may be advanced to its distal position. If the user wishes to return the safety shield to its releasably retained proximal position the shield is slid in a proximal direction and rotated clockwise, illustrated as direction W in FIG. 8A, until projections 61 abut against protuberances 45 indicating to the user that the shield is securely retained. This structure limits the amount of rotation required to release and retain the safety shield in its proximal position and also provide some tactile feel to the user regarding the status of the syringe. Two protuberances positioned, for example, about 90° from each other can also be used for limiting the rotation of the shield with respect to the collar to equal or less than 90°.

It is preferred that projections 61 on the safety shield be part of and aligned with axial ribs 62 which run the length of the safety shield so that after the safety shield is released from its proximal position and is advancing to its distal position rotation of the safety shield with respect to the syringe barrel will be resisted by the presence of rib 62 in recesses 43. Projections 61 are illustrated as being slightly larger than axial ribs 62 for the purpose of clearly teaching the invention. However, it is preferred, for molding and functional purposes, that the projection 61 be approximately the same size as axial rib 62. It is important to note that axial ribs 62 are not necessary to practice the present invention but are a desirable and preferable structural feature as will be explained in more detail hereinafter. As will be seen hereinafter, the angular position of ribs 62 will allow locking teeth 70 on the safety shield to contact a portion of the collar that is not interrupted by the recesses. This is important since in this preferred embodiment the elements will be aligned to provide maximum resistance to moving the safety shield from the distal locked position.

Proximal end 56 of safety shield 36 is characterized by a plurality of spaced apart stop blocks 64. Each stop block 64 includes an inwardly facing surface 66 and a radially aligned, distally facing stop surface 68. The inside diameter "H" defined by stop blocks 64 is less than the outer diameter "C" at proximal end 40 of locking collar 38. Thus, distally directed telescoped movement of safety shield 36 along syringe barrel 12 is positively limited by proximal end 40 of locking collar 38. In particular, the radially aligned distally facing stop surfaces 68 of stop blocks 64 will positively engage annular proximally facing end surface 49 of locking collar 38 to prevent proximal-to-distal removal of safety shield 36 from syringe barrel 12.

Figure 9A:
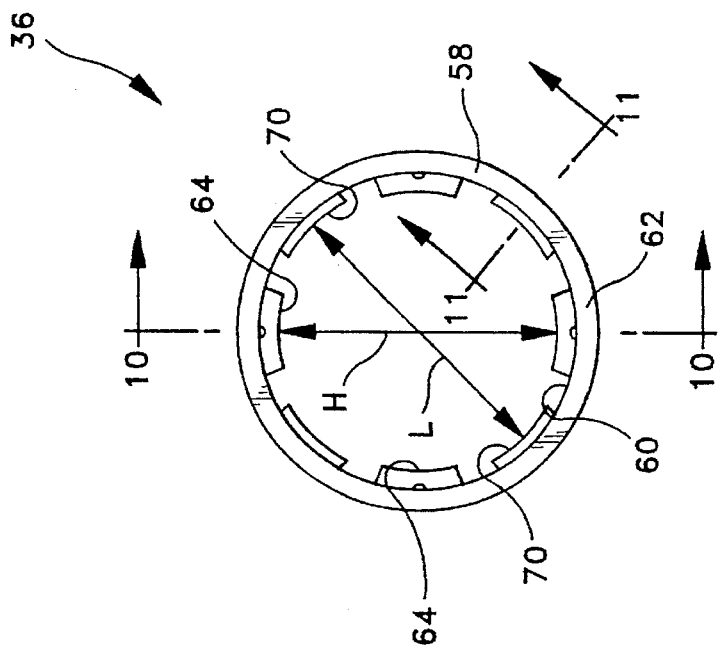
FIG. 9A is a proximal end elevational view of a safety shield in accordance with the subject invention.
Figure 12:
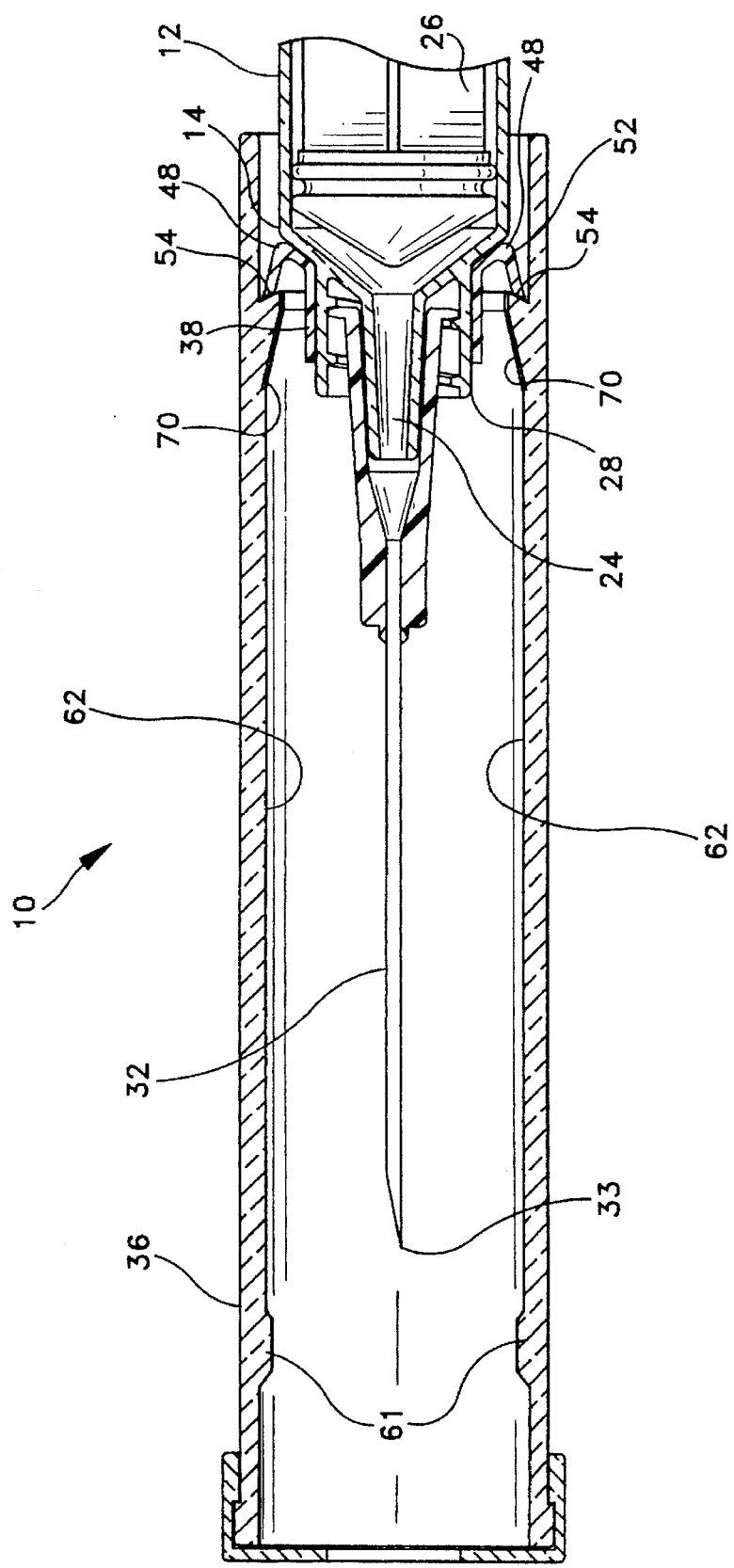
FIG. 12 is a side elevational view similar to FIG. 2 but showing the safety shield partly in section and in the distal locked position relative to the hypodermic syringe.

Safety shield 36 further includes a plurality of spaced apart locking teeth 70 which are disposed distally of stop blocks 64 by a distance "T" which is greater than distance "G" between stop surface 49 and the distal end of resilient lock wall 52 on collar 38. Locking teeth 70 are shaped to define a minor inside diameter "L" at locations closer to proximal end 56 of safety shield 36. Minor inside diameter "L" is less than major diameter "F" defined by resilient deflectable lock wall 52 of collar 38. Locking teeth 70 include proximal ends 71 which are aligned to a radius at an angle approximately equal to the angle of frusto-conical surface 54 at the extreme distal end of resilient deflectable lock 52 which in this preferred embodiment is approximately 30° as illustrated in FIG. 9.

Hypodermic syringe 10 is assembled by first sliding safety shield 36 over syringe barrel 12. Locking collar 38 then is slid onto syringe barrel 12, in a distal-to-proximal direction, such that barbs 46 bite into luer collar 28 to prevent subsequent proximal-to-distal removal of collar 38.

After use, and rotation of the safety shield to align projections 61 and recesses 43, safety shield 36 is telescoped in a distal direction over syringe barrel 12. Initial distal movement of safety shield 36 is controlled by contact between ribs 62 which pass through recesses 43 of collar 38. Locking teeth 70 then will engage and inwardly deflect frusto-conical locking wall 52 of locking collar 38, and enable continued distal advancement of safety shield 36 over syringe barrel 12. After sufficient distal movement, locking teeth 70 will move distally beyond frusto-conical deflectable locking wall 52 of locking collar 38. At this point, locking wall 52 will resiliently return toward an undeflected or less deflected condition defining an outside diameter "F" greater than the inside diameter "L" defined by locking teeth 70. As a result, re-exposure of needle cannula 32 is prevented by engagement between locking teeth 70 with the locking wall 52 of locking collar 38. The frusto-conical concave configuration of distal end 54 locking wall 52 and the corresponding configuration of proximal ends 71 of locking teeth 70 will urge frusto-conical locking walls 52 of locking collar 38 outwardly and tightly into safety shield 36, thereby further enhancing locking in response to proximal forces on safety shield 36. Because of surface 71 on the locking teeth and the configuration of the resiliently deflectable locking walls 52, a proximally directed force to the shield will cause the locking walls 52 to expand and more securely engage the locking teeth. Accordingly, increased force is met with increased resistance. This is an important feature of the invention. This locking engagement of teeth 70 with locking collar 38 can be accompanied by a clearly recognizable tactile and audible indication of complete locking of safety shield 36 as teeth 70 pass locking collar 38 and enable the resilient return of locking wall 52 toward a substantially undeflected condition. Removal of safety shield 36 in a distal direction is prevented by engagement of stop blocks 64 with the stop surface defined by proximal end 40 of locking collar 38.

Figure 13A:
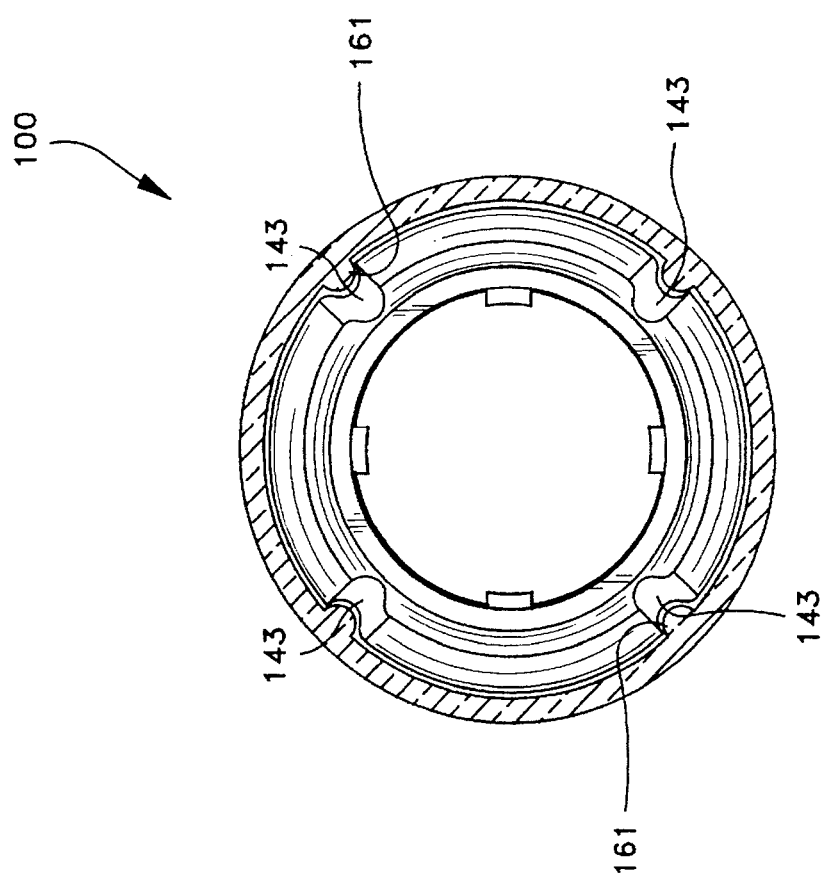
FIG. 13A is a cross-sectional view of an alternative syringe assembly having a modified collar which allows rotation of the safety shield in one direction only.
Figure 13B:
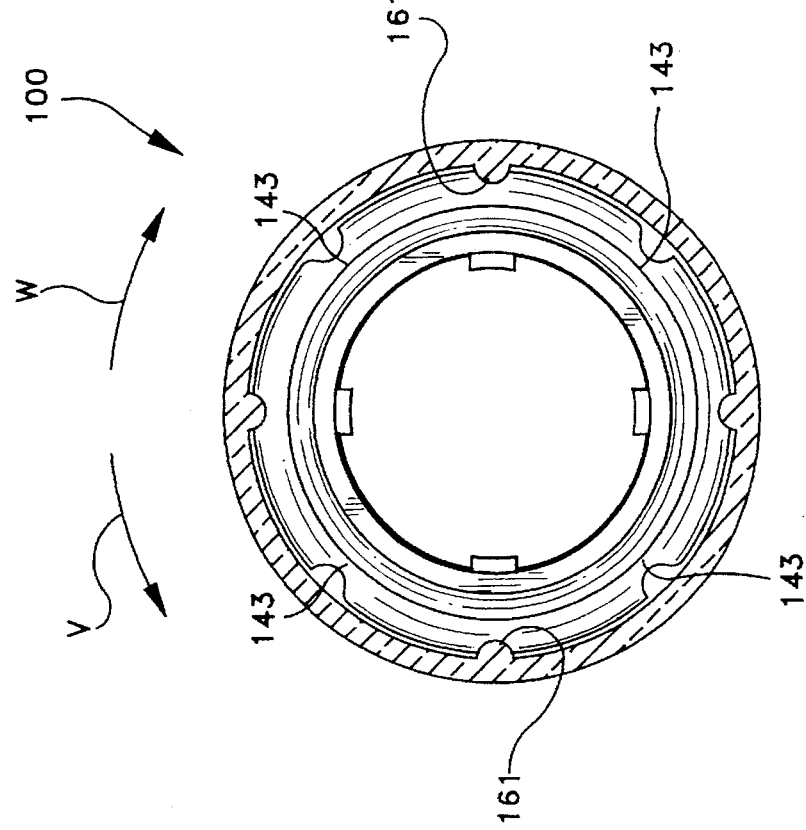
FIG. 13B is the syringe assembly of FIG. 13A illustrating the safety shield rotated with respect to the collar so that the projections on the safety shield align with the recesses on the collar to allow movement of the safety shield from its proximal position.

An alternative embodiment to the present invention is illustrated in FIGS. 13A and 13B. Except as noted, the embodiment of FIGS. 13A and 13B has substantially similar components, functioning in a similar way to the embodiments of FIGS. 1–12. The alternative embodiment illustrates that the present invention includes within its purview a variety of contours and shapes for the protuberances on the collar and the recesses in the collar which are used to retain the safety shield in the proximal position and to limit is rotational motion with respect to the collar. The alternate syringe assembly 100 includes safety shield 136 having four equally spaced inwardly directed projections 161 near the distal end of the safety shield. Collar 138 includes four equally radially inwardly directed recesses 143. Rather than using distinct radially directed protuberances such as protuberances 45 in the embodiment of FIGS. 1–12, the recesses 143 are asymmetrically shaped to stop or resist rotation of the safety shield in clockwise direction W with respect to the collar. With careful dimensioning and shaping of projections 161 and asymmetrical recesses 143 the interaction between the projections and the recesses can be made to resist counterclockwise rotation, direction as illustrated as direction V in FIG. 13A, of the safety shield with respect to the collar. It should be understood that restriction of the rotation of the safety shield with respect to the collar while the safety shield is in its proximal position is not necessary but is a desirable aspect of the present invention. Restriction of rotation of the safety shield as illustrated in FIGS. 13A and B when the projections are aligned with the recesses so that the shield can be advanced distally is desirable. This resistance prevents the user from overshooting the mark and needlessly manipulating the syringe while the needle is exposed. Combinations of asymmetrically-shaped recesses and protuberances can be used to achieve the desired degree of angular rotation of the shield and the tactile feel of the shield engaging the collar.

Although the prior art provides many syringes having safety shields and many structures to hold the safety shield in the extended needle protecting position and to releasably retain the safety shield in its proximal needle exposing position, there is still a need for simple, straight-forward, easy-to-manufacture syringe having a safety shield wherein both the extended and the retracted position of the safety shield are controlled by structure on the distal end of the syringe barrel using a structure that does not subject the safety shield and the syringe barrel to great stresses while the syringe is in storage with the safety shield in its proximal position with respect to the syringe barrel.

What is claimed is:

1. A safety syringe assembly comprising:
    a hypodermic syringe having a syringe barrel with opposed proximal and distal ends, said distal end of said syringe barrel having a needle cannula mounted thereto;
    a collar mounted around said syringe barrel, said collar including at least one radially inwardly directed recess;
    a safety shield positioned over said syringe barrel for telescoping movement from a proximal position where said needle cannula is exposed to a distal position where said safety shield protectively surrounds said needle cannula, said safety shield being rotatable with respect to said barrel when said safety shield is in said proximal position, said safety shield having an inside surface including at least one inwardly directed projection sized and positioned to pass through said recess in said collar when safety shield is rotated with respect to said barrel to align said projection and said recess and said safety shield is moved from said proximal position toward said distal position, said collar and said projection preventing movement of said safety shield from said proximal position when said projection and said recess are not aligned; and
    means for locking engagement of said collar and said safety shield for locking said safety shield in said distal position wherein said locking engagement can be achieved with only axial movement of said safety shield distally with respect to said barrel.

2. The safety syringe assembly of claim 1 wherein said at least one projection includes four substantially equally spaced projections and said at least one recess includes four substantially equally spaced recesses.

3. The safety syringe assembly of claim 1 wherein said collar includes at least one radially directed protuberance positioned to block motion of said projection as said shield is rotated with respect to said collar for limiting rotation to less than 360 degrees.

4. The safety syringe assembly of claim 3 wherein said at least one protuberance includes at least two protuberances positioned about 90 degrees from each other for limiting the rotation of said safety shield with respect to said collar to equal or less than 90 degrees.

5. The safety syringe assembly of claim 3 wherein said at least one protuberance includes four protuberances.

6. The safety syringe assembly of claim 1 wherein said means for locking includes said collar having a stop wall projecting outwardly from said syringe barrel and at least one deflectable lock wall projecting distally and outwardly from said collar; and
    said safety shield including at least one stop block projecting inwardly therefrom, said stop block being engageable with said stop wall of said collar for preventing removal of said safety shield from said syringe barrel when said shield is in said distal position, said safety shield further comprising at least one locking tooth dimensioned and disposed to generate inward deflection of said lock wall of said collar during said telescoping movement of said safety shield from said proximal position toward said distal position, said locking tooth being spaced distally from said stop block a sufficient distance to enable engagement of said lock wall and said stop wall of said collar between said locking tooth and stop block of said safety shield, and said locking tooth configured to lockably engage said deflectable lock wall to prevent proximal movement of said safety shield from its locked distal position.

7. The safety syringe assembly of claim 6 wherein said at least one projection on said safety shield is positioned on said safety shield so that when said safety shield is in said proximal position said at least one projection pushes against said lock wall until said safety shield is rotated with respect to said barrel to align said at least one projection and said at least one groove.

8. The safety syringe assembly of claim 7 wherein said syringe barrel includes a finger flange at said proximal end of said barrel and said safety shield contacting said finger flange when said safety shield is in said proximal position.

9. The safety syringe assembly of claim 1 wherein said at least one recess in said collar is shaped to prevent continual rotation of said safety shield in the same direction with respect to said collar after said projection in said safety shield is aligned with and in said recess in said collar.

10. The safety syringe assembly of claim 1 wherein said collar includes an inner circumferential surface comprising a plurality of inwardly and distally directed barbs for biting into the syringe barrel for preventing proximal-to-distal removal of said collar from said syringe barrel.

11. The safety syringe assembly of claim 6, wherein said deflectable lock wall is a continuous frusto-conically-shaped wall except for said at least one recess.

12. The safety syringe assembly of claim 6, wherein said deflectable lock wall of said collar comprises a plurality of independently deflectable spaced apart locking wall segments projecting distally and outwardly from said collar.

13. The safety syringe assembly of in claim 6, wherein said deflectable lock wall of said collar includes a generally concavely tapered distal end for generating outward deflection of said lock wall in response to proximally directed forces exerted thereon.

14. The safety syringe assembly of claim 13, wherein said concavely tapered distal end of said lock wall defines a frusto-conically-shaped surface inclined at an angle of approximately 30 degrees with a radius of said collar.

15. The safety syringe assembly of claim 13, wherein said locking tooth of said safety shield includes a proximal end tapered for generating outward deflection of said lock wall of said collar in response to proximally directed forces of said locking tooth on said deflectable lock wall.

16. The safety syringe assembly of claim 6, wherein said safety shield includes opposed proximal and distal ends, said at least one stop block comprises a plurality of circumferentially spaced stop blocks generally adjacent said proximal end of said safety shield, and wherein said at least one locking tooth comprises a plurality of circumferentially spaced locking teeth.

17. The safety syringe assembly of claim 6, wherein said locking tooth is ramped to generate inward deflection of said locking wall of said locking collar in response to distally directed telescoped movement of said safety shield from said proximal position on said syringe barrel to said locked distal position.

* * * * *